United States Patent
Suzuki

(10) Patent No.: US 7,457,452 B2
(45) Date of Patent: Nov. 25, 2008

(54) RADIOGRAPHIC IMAGE DIAGNOSIS DEVICE

(75) Inventor: Katsumi Suzuki, Kashiwa (JP)

(73) Assignee: Hitachi Medical Corporation, Tokyo (JP)

( * ) Notice: Subject to any disclaimer, the term of this patent is extended or adjusted under 35 U.S.C. 154(b) by 964 days.

(21) Appl. No.: 10/510,582

(22) PCT Filed: Apr. 10, 2003

(86) PCT No.: PCT/JP03/04552

§ 371 (c)(1),
(2), (4) Date: Oct. 8, 2004

(87) PCT Pub. No.: WO03/084404

PCT Pub. Date: Oct. 16, 2003

(65) Prior Publication Data

US 2005/0123094 A1 Jun. 9, 2005

(30) Foreign Application Priority Data

Apr. 10, 2002 (JP) ............................. 2002-107984

(51) Int. Cl.
*G06K 9/00* (2006.01)
*H05G 1/10* (2006.01)
*H01J 35/18* (2006.01)

(52) U.S. Cl. ...................... 382/132; 378/101; 378/140

(58) Field of Classification Search ................. 382/128, 382/129, 130, 131, 132, 133, 134; 378/4, 378/21–28, 46, 63, 90, 92, 98.4, 98.6, 98.9, 378/101, 140, 901; 424/9.5, 9.6, 9.7, 9.8; 250/370.09, 390.02

See application file for complete search history.

(56) References Cited

U.S. PATENT DOCUMENTS

| | | | | |
|---|---|---|---|---|
| 5,465,284 | A * | 11/1995 | Karellas | 378/62 |
| 6,272,207 | B1 * | 8/2001 | Tang | 378/149 |
| 6,900,442 | B2 * | 5/2005 | Zur | 250/370.11 |
| 6,950,492 | B2 * | 9/2005 | Besson | 378/5 |

FOREIGN PATENT DOCUMENTS

JP 5-281360 10/1993
JP 2000-175892 6/2000

* cited by examiner

*Primary Examiner*—Abolfazl Tabatabai
(74) *Attorney, Agent, or Firm*—Antonelli, Terry, Stout & Kraus, LLP.

(57) ABSTRACT

A correction table unit (5) contains correction tables for correcting output values of image data of the first image, the second image, . . . , the n-th image successively output from an X-ray plane detector (4) of a radiographic image diagnosis device and having different output rise characteristics. After correction of the image data, the second image data is subtracted from the first image data, . . . , and the n-th image data is subtracted from the first image data by a subtraction unit (8). As a result, a subtraction image, i.e., an angiographic image is displayed on display means (9). Since the affect of the different rise characteristics of each image data is eliminated, it is possible to obtain an angiographic image having a uniform background brightness and a preferable contrast.

12 Claims, 3 Drawing Sheets

RADIOGRAPHIC IMAGE DIAGNOSIS DEVICE

FIELD OF THE INVENTION

The present invention relates to an X-ray diagnosis apparatus having an X ray flat panel detector and in particular, relates to an X-ray diagnosis apparatus which is provided with a function of correcting a low output characteristic at an initial stage of image taking by an X ray flat panel detector.

BACKGROUND ART

These days X-ray diagnosis apparatuses use as their X ray detectors an X ray flat panel detector. The X ray flat panel detector is constituted by a scintillator (for example, made of cesium iodide (CsI)) which converts X ray transmitted through an object to be examined into light, photodiodes (for example, made by amorphous silicon (a-Si)) which converts the light output from the scintillator into electric charge and switching elements such as, for example, thin film transistors (TFT) which read the electric charge, and, for example, has an active area of 30×40 $cm^2$ and 7,400,000 pixels.

However, as referred to, for example, in R. L. Weisfield et al. "High Performance Amorphous Silicon Image Sensor for X-ray Diagnostic Medical Imaging Application" (SPIE vol. 3659, Medical Imaging 1999, part of the SPIE Conference on Physics of Medical Imaging, San Diego, Calif., February 1999 pp 307-317), since the photo diodes in such X ray flat panel detector are not saturated at the initial stage of the image taking, the output thereof shows lower in comparison with when the photo diodes are saturated. For this reason when the imaging is performed successively from the initial stage thereof, the display brightness shows dark at the initial stage and gradually becomes bright.

When an angiographic detection is performed with such X-ray diagnosis apparatus, at the same time when contrast medium is injected to the object X ray is for the first time irradiated to the object, then X ray is successively irradiated to the object with a predetermined interval and the image data at respective moments are successively output from the X ray detector. In this instance, by making use of a first image data which is output first as a mask image and by subtracting from image date after second ones, only a blood vessel image where the contrast medium is injected is extracted and such as constriction of blood vessel is diagnosed from the image.

Namely, for the same X ray dose, the following tendency is observed that the signal value of the image data taken first which is used as the-mask image shows the lowest value and the signal values taken second, third . . . , which are used as live images successively increase toward the saturation. However, in the field of X ray detection, it is not preferable in view of X ray exposure of an object to irradiate X ray to the object prior to image taking irradiation.

FIG. 5 shows a build up output characteristic diagram of an X ray flat panel detector wherein the abscissa is image number according to output order and the ordinate is relative height of the output signal. In FIG. 5, symbols corresponding to letters a~g show different X ray doses (a>b>c>d>e>f>g) irradiated to the same X ray flat panel detector. The image number according to output order shows image taking order by the same X ray flat panel detector, in that first image, second image, third image, . . . , tenth image.

Since the X ray flat panel detector shows the build up output characteristic as shown in FIG. 5, the output values in the regions other than the contrast medium of the image data taken first which is used as the mask image and of the image data taken second and thereafter which are used as live images are different, therefore, even if the subtraction processing is performed, the regions other that the contrast medium can not sometimes be sufficiently subtracted, as a result, difference in brightness level of the background portion in the subtraction images which are used for the angiographic detection occurs and the contrast of the subtraction images is reduced, which causes a problem.

An object of the present invention is to provide an X-ray diagnosis apparatus which eliminates influences of inherent low output characteristic, namely, delay in output build up of an X ray flat panel detector in the X-ray diagnosis apparatus and permits to obtain subtraction images, namely, angiographic images of desirable contrast.

Another object of the present invention is to provide an X-ray diagnosis apparatus which eliminates influences of inherent low output characteristic of an X ray flat panel detector in the X-ray diagnosis apparatus and permits to obtain X ray images of uniform brightness which facilitates comparison observation.

DISCLOSURE OF THE INVENTION

A principle of the present invention is to match one of a build up output characteristic of, for example, a first image data value which is output from an X ray detector in an X-ray diagnosis apparatus and is used as a mask image and of a build up output characteristic of a second image data value and thereafter which is used as a live image with the other, and thereafter, subtraction processing of the both is performed, thereby, an influence due to different build up output characteristics of the respective images is eliminated and desirable subtraction images can be obtained.

More specifically, in the present invention, for example, the output data value of the tenth image shown in FIG. 5 when the inherent initial low output build up characteristic of the X ray flat panel detector is saturated is used as a reference and an output data value correction table for the respective first, second, . . . , nth images (n is an integer more than 1) is prepared in advance and stores the same in a memory, and when taking X ray images and display the same, prior to executing the subtraction processing for obtaining subtraction images, at first, the image data successively output from the X ray flat panel detector are corrected according to the output order by making use of correction tables corresponding to the order which are prepared in advance and stored in the memory, thereafter, by subtracting the corrected mask image data value from the respective corrected live image data values, thus the subtraction images of desirable contrast are obtained.

Further, according to another aspect of the present invention, for example, the output data value of the tenth image as shown in FIG. 5 when the inherent initial low output build up characteristic of the X ray flat panel detector is saturated is used as a reference and an output data value correction table for the respective first, second, . . . , nth images (n is an integer more than 1) is prepared in advance and stores the same in a memory, and when taking X ray images and display the same, after correcting the respective image output data by making use of the correction tables and by outputting the corrected image output data on a display, X ray images of uniform brightness which facilitates comparison observation are obtained.

BEST MODES FOR CARRYING OUT THE INVENTION

Herein below, an embodiment of the present invention will be explained with reference to drawings.

Figure 1:
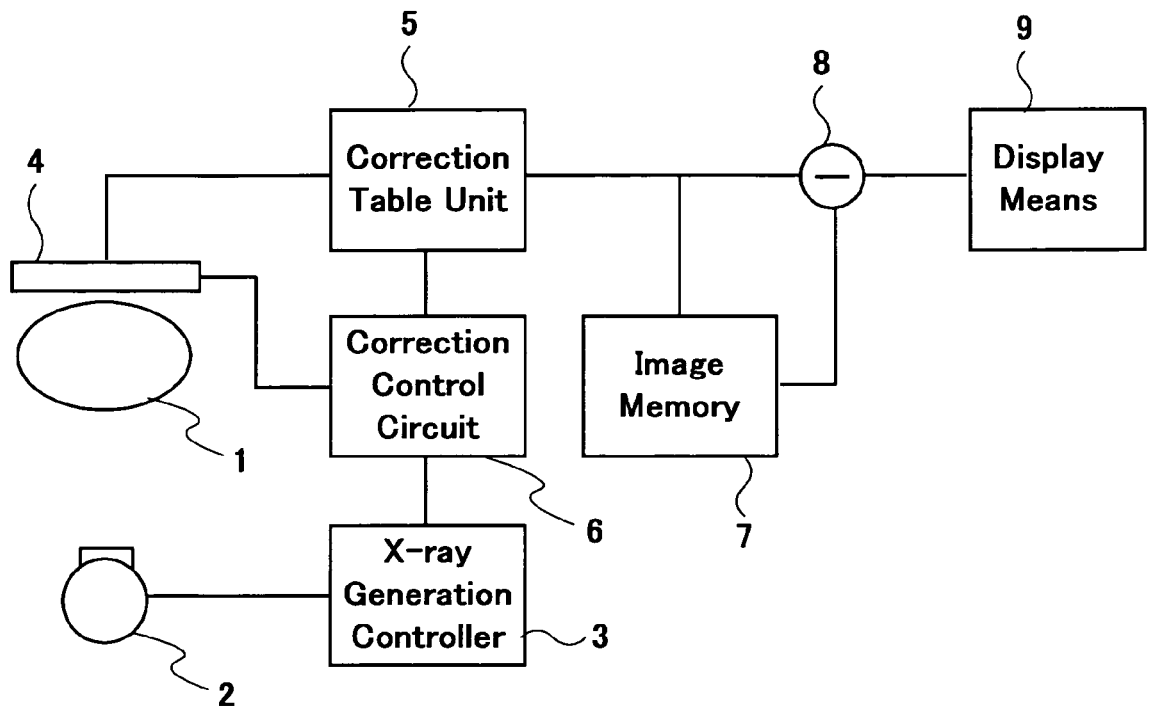
FIG. 1 is a block diagram showing an outline structure representing an embodiment of an X-ray diagnosis apparatus according to the present invention.

FIG. 1 is a block diagram showing an outline structure representing an embodiment of an X-ray diagnosis apparatus with an X ray flat panel detector according to the present invention.

As shown in FIG. 1, the X-ray diagnosis apparatus according to the present embodiment is provided with an X ray source 2 which irradiates X ray to an object 1, an X ray generation controller 3 which controls the irradiation of X ray from the X ray source 2 to the subject 1, an X ray flat panel detector 4 which detects X ray transmitted through the subject 1 and outputs as an image signal, a correction table 5 having a plurality of correction tables which correspond to the output order of image data representing the image signals successively output from the X ray flat panel detector 4, a correction control circuit 6 which controls the X ray generation controller 3 and the X ray flat panel detector 4 and selects from the correction table 5 a table corresponding to a image data representing the image signal output from the X ray flat panel detector 4, an image memory 7 which stores the image signal output first from the X ray flat panel detector 4 and corrected by the correction table 5 as a mask image data, a processor 8 which performs a subtraction process between the corrected image data successively output from the X ray flat panel detector 4 and corrected through the correction table 5 and the mask image data stored in the image memory 7 and a display means 9 which displays the image data subjected to the subtraction process by the processor 8, in that subtraction images.

Now, an operation of the X-ray diagnosis apparatus according to the present embodiment will be explained.

At the same time when an injection of contrast medium to the subject begins, the correction control circuit 6 issues a command to the X ray generation controller 3 to irradiate X ray from the X ray source 2 and further issues a command to fetch image data from the X ray flat panel detector 4 in synchronism with the irradiated X ray. In response to the command from the correction control circuit 6, the image data output first from the X ray flat panel detector 4 is sent to the correction table 5. When the correction table 5 judges that the image data sent from the X ray flat panel detector 4 is the image data output first according to a signal from the correction control circuit 6, selects a table for correcting the first image data, corrects the image data value based on the correction table and stores the same in the image memory 7.

Figure 2:
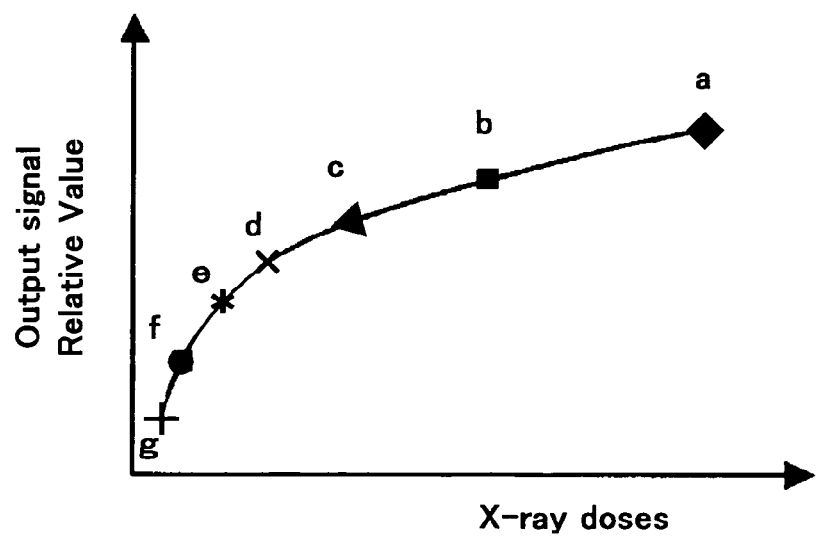
FIG. 2 is a view for explaining characteristic of a first image data, which is output from an X ray flat panel detector 4 in FIG. 1 wherein the abscissa is X ray doses and the ordinate is relative values of output signal height corresponding to the doses.

FIG. 2 is a characteristic curve diagram showing output characteristic of first image data output from the X ray flat panel detector 4 with respect to transmitted doses, wherein the abscissa is X ray doses and the ordinate is relative values of output signal. The plotted points in FIG. 2 correspond to relative output values with respect to seven X ray doses for first images, and based on these points, an approximation curve is formed for preparing the correction table for the first image. The approximation curve is determined by making use of generally known method, and the approximation curve as shown in FIG. 2 is calculated according to logarithmic approximation.

Figure 3:
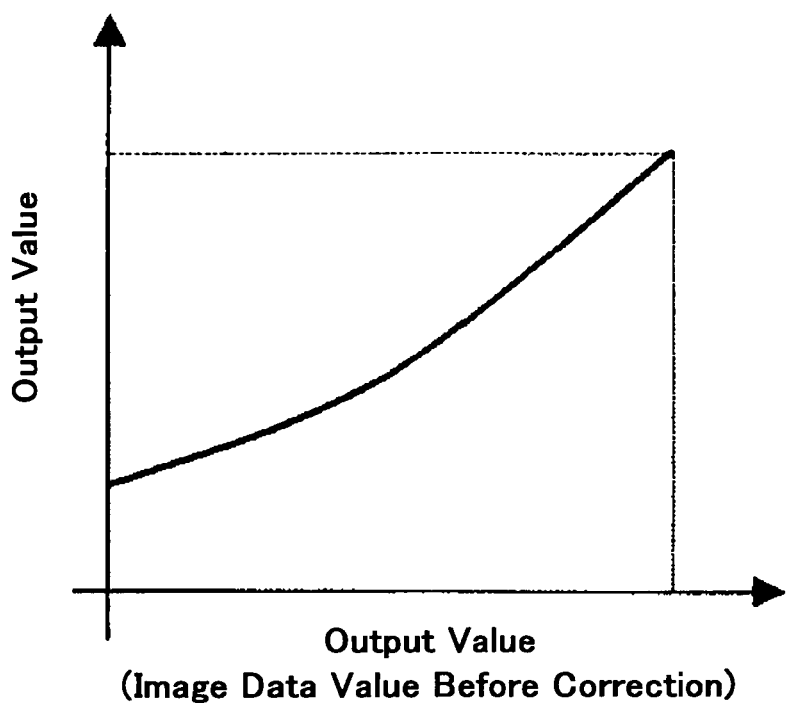
FIG. 3 is a diagram of characteristic curve showing a correction table stored in a correction table 5 in FIG. 1 for correcting a first image data output from an X ray flat panel detector 4 and used as a mask image.

FIG. 3 is a diagram of characteristic curve showing a correction table for correcting a first image data output from an X ray flat panel detector 4 wherein the abscissa is input values (image data values before correction) and the ordinate is output values (image data values after correction). After calculating correction amounts for the respective image data values according to the approximation curve determined in FIG. 2, the table for correcting first output image data from the X ray flat panel detector 4 is prepared. In FIG. 3 the table is set in such a manner that the lower the image data values are, the higher the image data after correction are.

Figure 4:
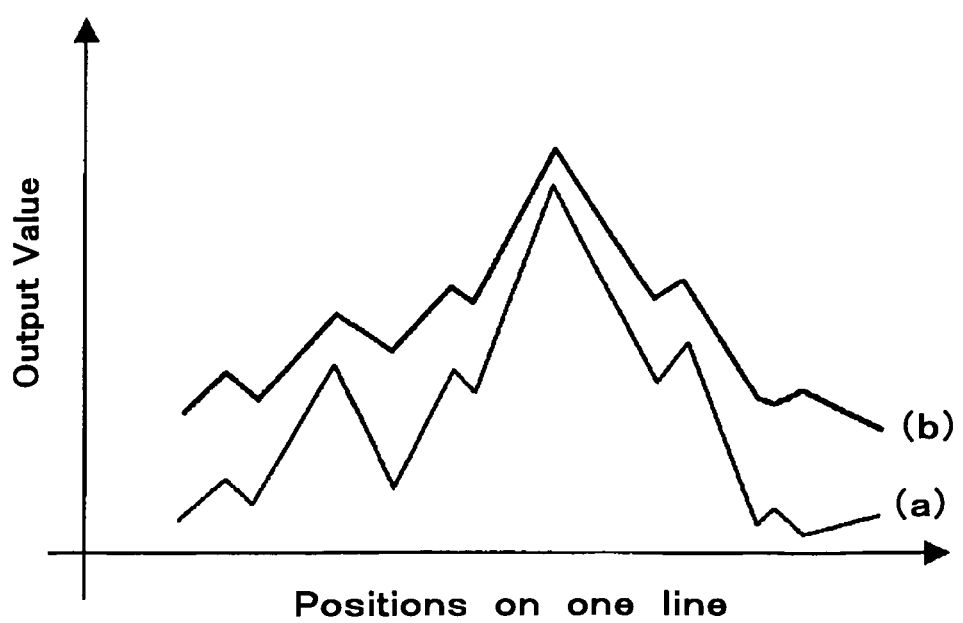
FIG. 4 is graphs showing output values on a certain one line of a first image data before and after correcting the same with the correction table as shown in FIG. 3.

FIG. 4 is characteristic line diagram showing output values on a certain one line of a first output image data before correction and after correction with the correction table as shown in FIG. 3 wherein the abscissa indicates positions on the one line and the ordinate indicates output values, and (a) represents characteristic line diagram before correction and (b) represents characteristic line diagram after correction.

Through the use of the correction table as shown in FIG. 3, the first image output from the X ray flat panel detector 4 is corrected from the output value distribution represented by the characteristic line diagram before correction (a) as shown in FIG. 4 to the distribution represented by the characteristic line diagram after correction (b). As seen from FIG. 4, it is understood that the output values at the portions where delay of output build up is significant due to non-saturation are corrected greatly.

The corrected first output image data is once stored in the image memory 7. Subsequently, in response to the command from the correction control circuit 6, when the second image data is output from the X ray flat panel detector 4, the correction control circuit 6 selects from the table 5 a table for correcting the second output image data to execute the correction. The correction table used in this instance is prepared in the same manner when the correction table for the first image was prepared. The second output image data corrected by the correction table 5 is subjected to subtraction process through the processor 8 by the corrected first image data stored in the image memory 7, thereby, regions other than the region where the contrast medium is injected are erased, and an image in which the blood vessel image stands out where the contrast medium is injected is displayed on the display means 9 and based on the displayed image, diagnosis is performed.

The variable components in the output characteristic of the image data of third and thereafter output from the X ray flat panel detector 4 are removed in the same manner as above, thus on the display means 9 blood vessel images having desirable contrast and uniform background brightness are always displayed.

Figure 5:
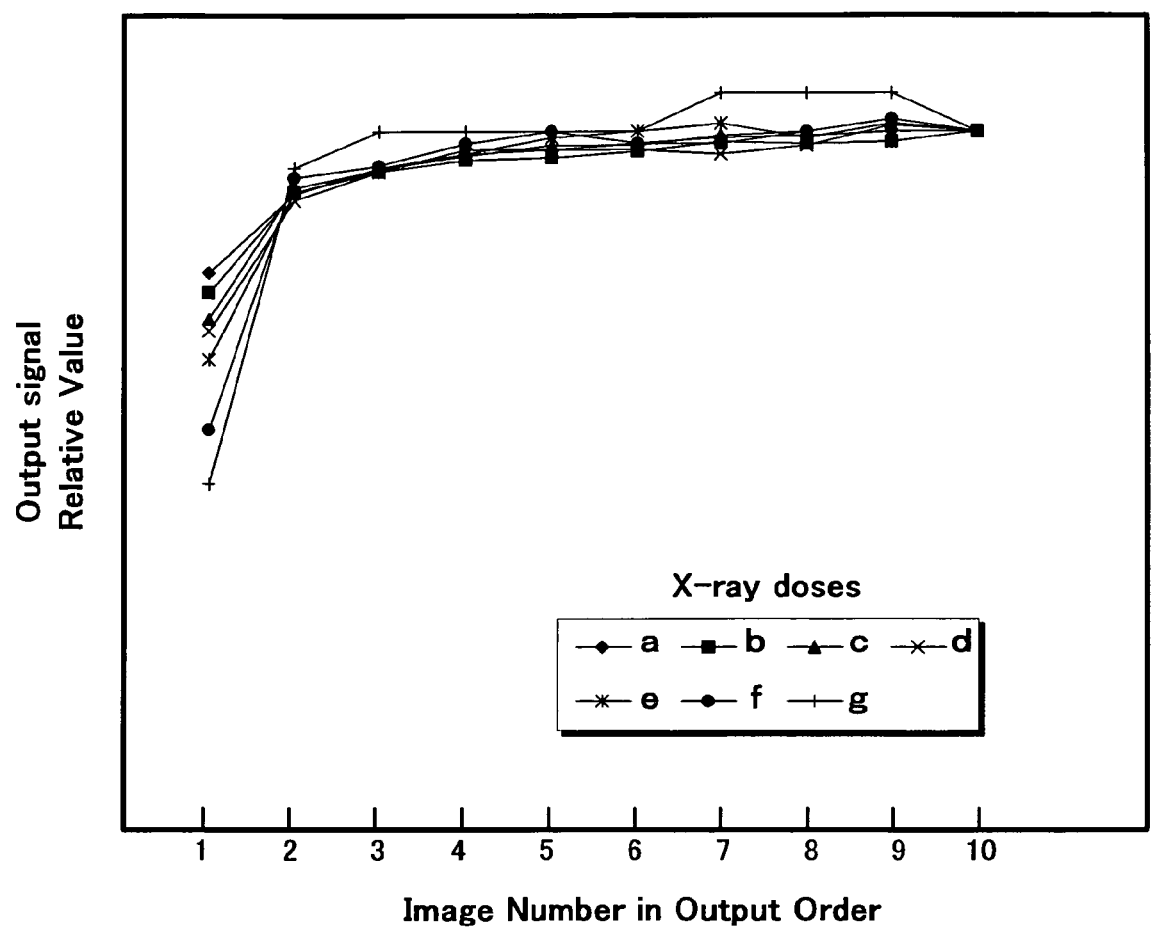
FIG. 5 is a diagram of characteristic curves showing relative values of output signal height from a first image to a tenth image of the X ray flat panel detector in FIG. 1 using X ray doses as the parameter.

Further, in the above embodiment, although, an example was explained of preparing a correction table in which image data values (tenth output image in FIG. 5) when the output variation of the X ray flat panel detector substantially disappears due to saturation of the capacitor portions of the photo diodes contained therein are used as a reference, the correction table can be prepared while using the first output image as a reference and matching the output image thereafter to the first output image data value.

Further, each of the respective correction tables for the first, second, ..., nth image data stored in the correction table 5 can be prepared in plural number in advance based on several parameters such as irradiation X ray doses, frame rate representing number of photographing per unit time, gain of the X ray flat panel detector which is varied depending on target photographing portions and image taking mode such as high image quality mode and high speed image collection mode, and still further, the respective reference tables can be used while modifying each time based on the above parameters.

Still further, in the above, the subtraction process of second image data—first image data, third image data—first image data, ..., nth image data—first image data through the processor 8 has been explained, however, in the processor 8 subtraction process of n–(n–1), n–(n–2), ..., n–2 can be executed with respect to the respective image data after correction.

Still further, in the above embodiment, an example of applying subtraction process on the corrected images has been explained, however, without performing the subtraction in the processor 8 the corrected images can be displayed as they are on the display means 9. Since the brightness of the corrected images obtained in the above manner is uniform, images which facilitates comparison observation can be provided Heretofore, the embodiments according to the present invention have been explained with reference to the drawings, however, the present invention does not limited to the embodiments, but can be practiced by modifying the same within the gist of the present invention.

INDUSTRIAL APPLICABILITY

The X-ray diagnosis apparatus with the X ray flat panel detector according to the present invention, in which X ray is irradiated to an object in plurality of times in a predetermined interval, a plurality of X ray images are taken and subtraction process is executed between these plurality of X ray image data and which is useful for obtaining subtraction images having desirable contrast and is, in particular, suitable for angiographic image detection.

The invention claimed is:

1. An X-ray diagnosis apparatus comprising: an X ray source which irradiates X ray to an object to be examined in a plurality of times with a predetermined time interval; an X ray flat panel detector which detects X ray each time transmitted through the subject and outputs the same as image data; a correction table which stores a characteristic of X ray dose versus output signal height of the X ray flat panel detector with respect to a first, second, third, ..., nth (n is an integer more than 1) image data output from the X ray flat panel detector; and a processor which executes subtraction process of at least the second image data value—the first image data value, the third image data value—the first image data value, ..., the nth image data value—the first image data value, wherein the subtraction process in the processor is executed after matching one of the characteristic of X ray dose versus output signal height of the image data to be subtracted and the characteristic of X ray dose versus output signal height of the image data to subtract to the other.

2. An X-ray diagnosis apparatus comprising: an X ray source which irradiates X ray to an object to be examined in a plurality of times with a predetermined time interval; an X ray flat panel detector which detects X ray each time transmitted through the subject and outputs the same as image data; a correction table which stores tables for eliminating respective characteristic differences of X ray dose versus output signal height of the X ray flat panel detector with respect to a first, second, third, ..., nth (n is an integer more than 1)image data output from the X ray flat panel detector; a processor which executes subtraction process of at least the second image data value—the first image data value, the third image data value—the first image data value, ..., the nth image data value—the first image data value with respect to the respective image data corrected through the correction table and outputs subtraction images; and a display which displays the output data from the processor as images.

3. An X-ray diagnosis apparatus according to claim 2, wherein the respective correction tables are set in such a manner that for a comparatively low X ray doses a comparatively large correction is added and for comparatively high X ray doses a comparatively small correction is added.

4. An X-ray diagnosis apparatus according to claim 2, wherein the respective correction tables are modified by at least one of frame rate, gain of the X ray flat panel detector and image taking mode.

5. An X-ray diagnosis apparatus according to claim 2, wherein the output correction amount of the respective correction tables for the first, second, third, ..., nth image data are set so as to decrease gradually.

6. An X-ray diagnosis apparatus according to claim 2, wherein the image data corrected by the respective correction tables are directly displayed on the display not through the processor.

7. An X-ray diagnosis apparatus comprising: an X ray source which irradiates X ray to an object to be examined in a plurality of times with a predetermined time interval; an X ray flat panel detector which is disposed to face the X ray source, detects every plurality of times X ray transmitted through the subject and outputs the same as image data; and display means which displays the respective image data output every plurality of times from the X ray flat panel detector, further comprising a storage means which stores respective input X ray versus output signal characteristics of the X ray flat panel detector being associated with image data output every plurality of times from the X ray flat panel detector; correction means which reads out the input X ray versus output signal characteristics of the X ray flat panel detector for the plurality of times stored in the storage means and corrects the image data for a predetermined time among the plurality of times by the read out input X ray versus output signal characteristics of the X ray flat panel detector for the plurality of times; and means for displaying the image data corrected by the correction means on the display means and for controlling the same.

8. An X-ray diagnosis apparatus according to claim 7, wherein the correction means corrects the image data obtained at one time among the plurality of times based on the input X ray versus output signal characteristic of the X ray flat panel detector associated with the image data and the input X ray versus output signal characteristic of the X ray flat panel detector associated with the image data obtained at another time.

9. An X-ray diagnosis apparatus according to claim 7, wherein the correction means selects an input X ray versus output signal characteristic of the X ray flat panel detector stored in the storage means in such a manner that for a comparatively low X ray doses a comparatively large correction is added and for comparatively high X ray doses a comparatively small correction is added.

10. An X-ray diagnosis apparatus according to claim 7, wherein the respective input X ray versus output signal characteristics of the X ray flat panel detector stored in the storage means are modified by at least one of frame rate, gain of the X ray flat panel detector and image taking mode.

11. An X-ray diagnosis apparatus according to claim 7, wherein the respective input X ray versus output signal characteristics of the X ray flat panel detector stored in the storage means are set in such a manner that the output correction amount of the respective correction tables with respect to the respective image data obtained for the plurality of times decreases gradually.

12. An X-ray diagnosis apparatus according to claim 7, further comprising means for performing subtraction process between the image data obtained at one time among the plurality of times and the image data obtained at another time, wherein the display means displays the processed result performed by the subtraction process means as images.

* * * * *